United States Patent
Osorio et al.

(10) Patent No.: US 6,671,556 B2
(45) Date of Patent: *Dec. 30, 2003

(54) VAGAL NERVE STIMULATION TECHNIQUES FOR TREATMENT OF EPILEPTIC SEIZURES

(76) Inventors: Ivan Osorio, 4005 W. 124th St., Leawood, KS (US) 66209; Mark G. Frei, 2513 Via Linda Dr., Lawrence, KS (US) 66047

(*) Notice: Subject to any disclaimer, the term of this patent is extended or adjusted under 35 U.S.C. 154(b) by 143 days.

This patent is subject to a terminal disclaimer.

(21) Appl. No.: 10/053,425

(22) Filed: Nov. 9, 2001

(65) Prior Publication Data

US 2002/0072782 A1 Jun. 13, 2002

Related U.S. Application Data

(63) Continuation of application No. 09/302,516, filed on Apr. 30, 1999, now Pat. No. 6,341,236.

(51) Int. Cl.[7] .......................... A61N 1/18; A61N 1/362
(52) U.S. Cl. ............................................. 607/45; 607/9
(58) Field of Search ........................................ 607/45, 9

(56) References Cited

U.S. PATENT DOCUMENTS

| | | |
|---|---|---|
| 4,628,942 A | 12/1986 | Sweeney et al. |
| 4,649,936 A | 3/1987 | Ungar et al. |
| 4,702,254 A | 10/1987 | Zabara |
| 4,867,164 A | 9/1989 | Zabara |
| 5,025,807 A | 6/1991 | Zabara |
| 5,052,388 A | 10/1991 | Sivula et al. |
| 5,330,508 A | 7/1994 | Gunderson |
| 5,562,711 A | 10/1996 | Yerich et al. |
| 5,713,923 A | 2/1998 | Ward et al. |
| 5,928,272 A | 7/1999 | Adkins et al. |
| 5,995,868 A | 11/1999 | Dorfmeister et al. |
| 6,018,682 A * | 1/2000 | Rise .............................. 607/45 |
| 6,337,997 B1 * | 1/2002 | Rise ............................... 607/3 |
| 6,374,140 B1 * | 4/2002 | Rise ............................ 600/544 |

OTHER PUBLICATIONS

Jones et al., "Heart Rate Responses to Selective Stimulation of Cardiac Vagal C Fibers in Anaesthetized Cats, Rats and Rabbits," J. Physiol (London) 489.1:203–214 (1995).

Jalife J. Antzelevitch C., "Pacemaker Annihilation: Diagnostic and Therapeutic Implications," Am Heart J 100:128–130 (1980).

Frei et al., "Effects of Vagal Stimulation on Human EEG," AES Proceedings, p. 200 (1998).

Asconape et al., "Early Experience with Vagus Nerve Stimulation for the Treatment of Epilepsy; Cardiac Complications," AES Proceeding, p. 193 (1998).

(List continued on next page.)

*Primary Examiner*—Jeffrey R. Jastrzab
(74) *Attorney, Agent, or Firm*—Banner & Witcoff, Ltd.

(57) ABSTRACT

The present invention uses electrical stimulation of the vagus nerve to treat epilepsy with minimized or no effect on the heart. Treatment is carried out by an implantable signal generator, one or more implantable electrodes for electrically stimulating a predetermined stimulation site of the vagus nerve, and a sensor for sensing characteristics of the heart such as heart rate. The heart rate information from the sensor can be used to determine whether the vagus nerve stimulation is adversely affecting the heart. Once threshold parameters are met, the vagus nerve stimulation may be stopped or adjusted. In an alternative embodiment, the invention may include a modified pacemaker to maintain the heart in desired conditions during the vagus nerve stimulation. In yet another embodiment, the invention may be simply a modified pacemaker having circuitry that determines whether a vagus nerve is being stimulated. In the event that the vagus nerve is being stimulated, the modified pacemaker may control the heart to maintain it within desired conditions during the vagus nerve stimulation.

69 Claims, 11 Drawing Sheets

OTHER PUBLICATIONS

Mark V. Kamath, "Neurocardiac Responses to Vagoafferent Electrostimulation in Humans," PACE, vol. 15, Oct. (1992) p. 1581.

Handforth et al., "Vagus Nerve Stimulation Therapy for Partial Onset Seizures: A Randomized Active Control Trial," J. Neurology, vol. 5, pp. 48–55 (1998).

Han et al., "Probably Mechanisms of Action of Vagus Nerve Stimulation in Humans with Epilepsy: Is the Heart the Window into the Brain?" AES Processing, p. 83 (1997).

Frei et al., "Effect of Vagal Stimulation on Human ECG," Abstract from the Annual Meeting of the American Epilepsy Society, vol. 39, Supp. 6 (1998).

Salinskey et al, "Vagus Nerve Stimulation Has No Effect on Awake EEG Rhythms in Humans," J. Epilespia, vol. 34(2), pp. 229–304 (1993).

Michael H. Chase et al., "Afferent Vagal Stimulation neurographic Correlates if Induced EEG Synchronization and Desynchronization," Brain Research pp. 236–249 (1967).

Chase et al., "Cortical and Subcortical Patterns of Response to Afferent Vagal Stimulation," Experimental Neurology, vol. 16, pp. 36–49 (1966).

Jalife J. Anzelecitch C., "Phase Resetting and Annihilation of Pacemaker Activity in Cardiac Tissue," Science 206:695–697 (1979).

Windfree AT., "Sudden Cardian Death: A Problem in Topology," Sci Am, 248:144–161 (1983).

Ruda, Anti, "A Real–Time Microprocessor QRS Detector with a 1–ms Timing Accuracy for the Measurement of Ambulatory HRV," IEEE Transactions on Biomedical Engineering, vol. 44, Nos. 3, pp. 159–167 (Mar. 1997).

Accornero et al., "Selective Activation of Peripheral Nerve Fibre Groups of Different Diameter by Triangular Shaped Pulses," J. Physiol. pp. 539–560 (1977).

Bures et al., "Electrophysiological Methods n Biological Research" Academic Press New York, London pp. 338–339 (3rd ed. 1967).

* cited by examiner

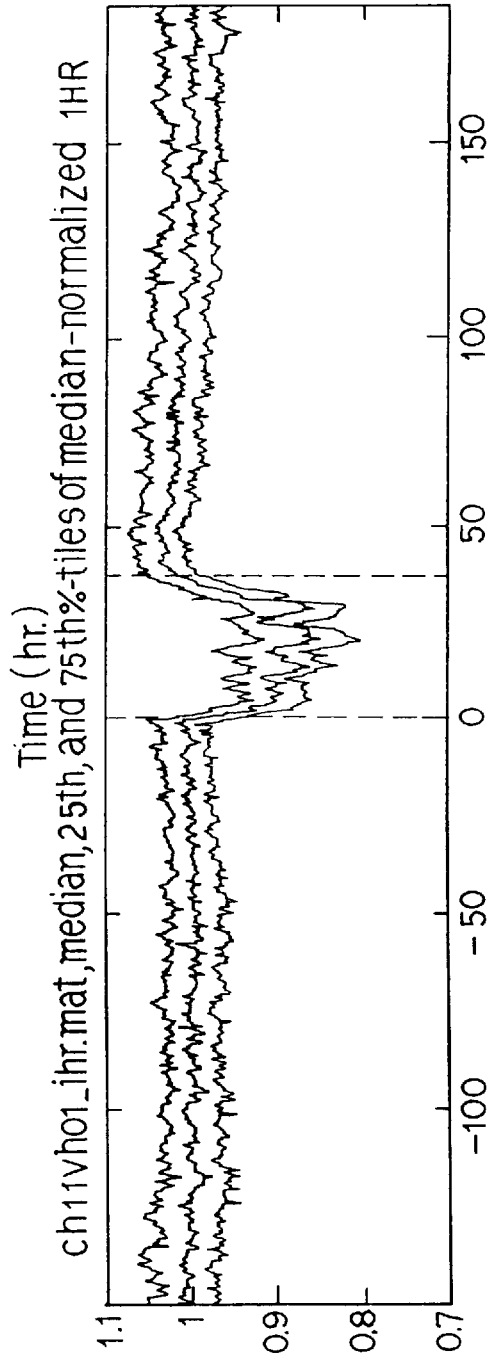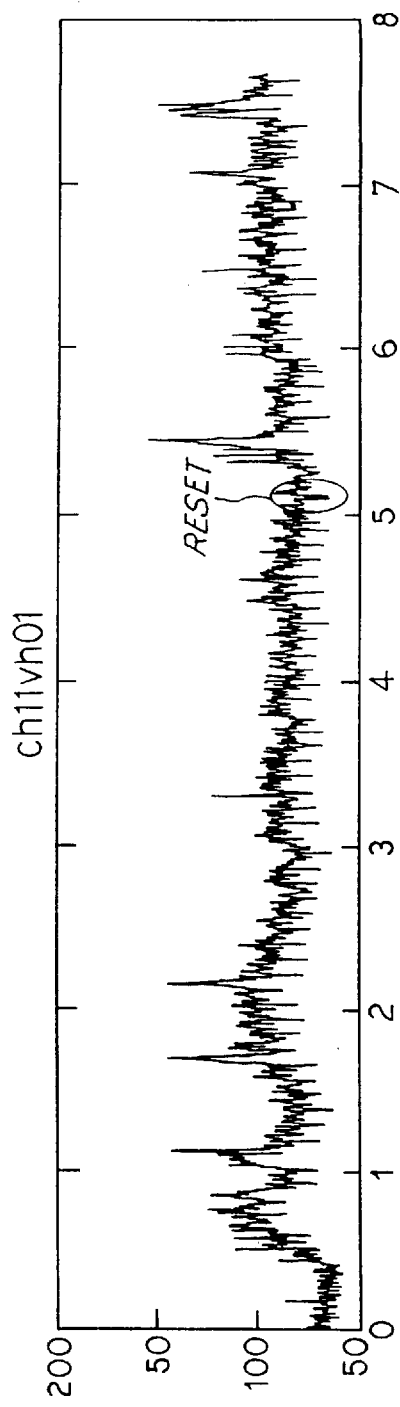

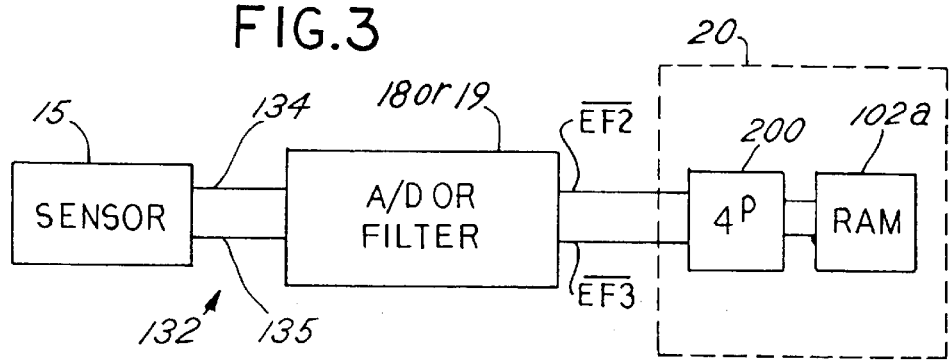
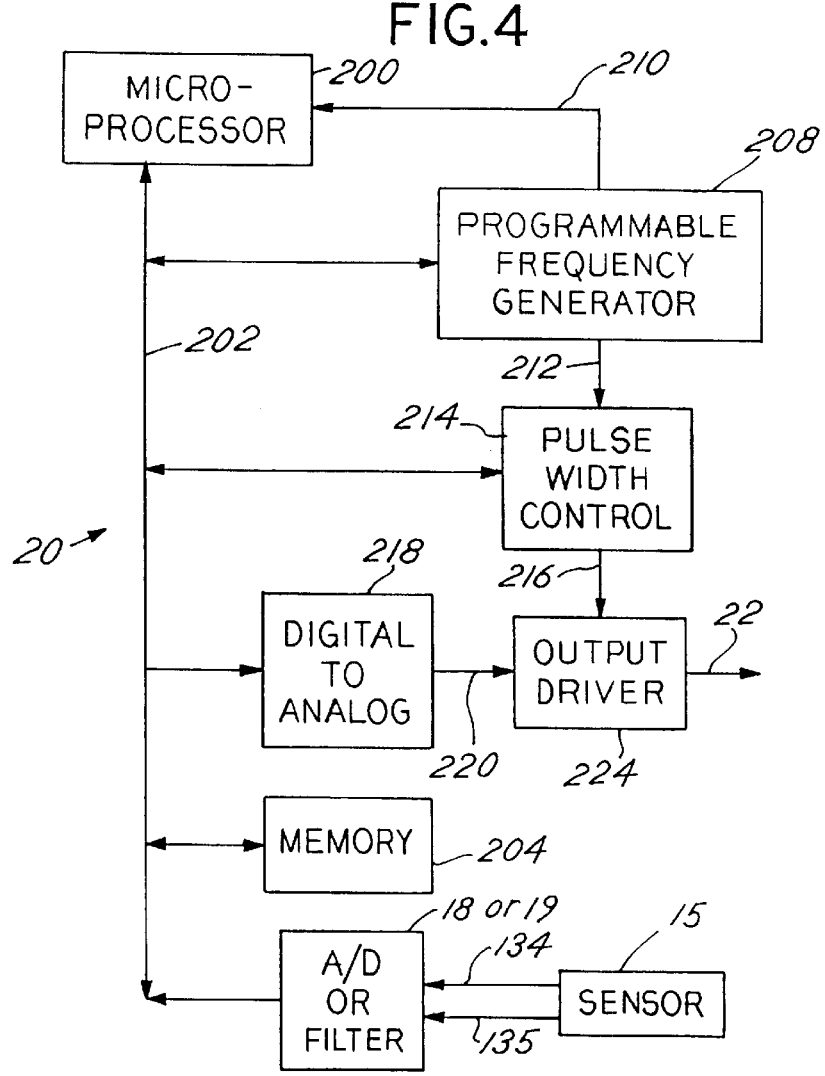

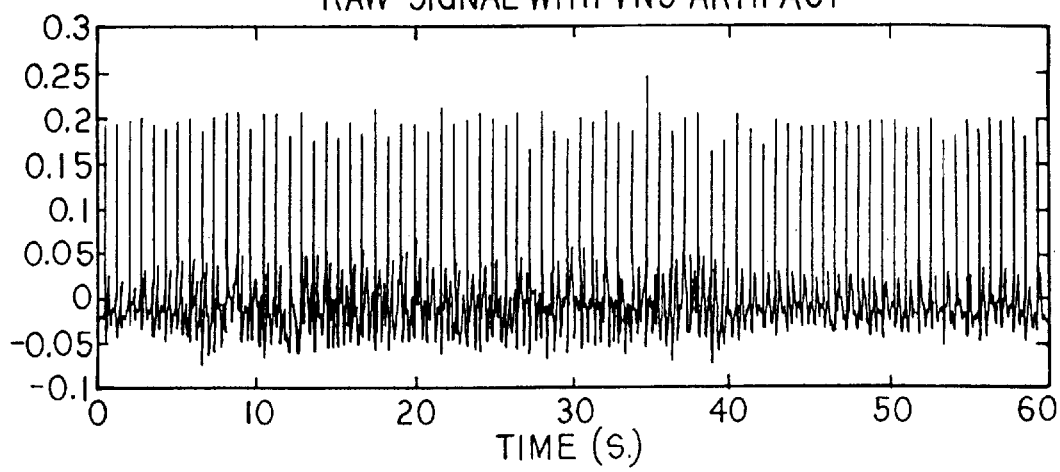
FIG.11A — RAW SIGNAL WITH VNS ARTIFACT
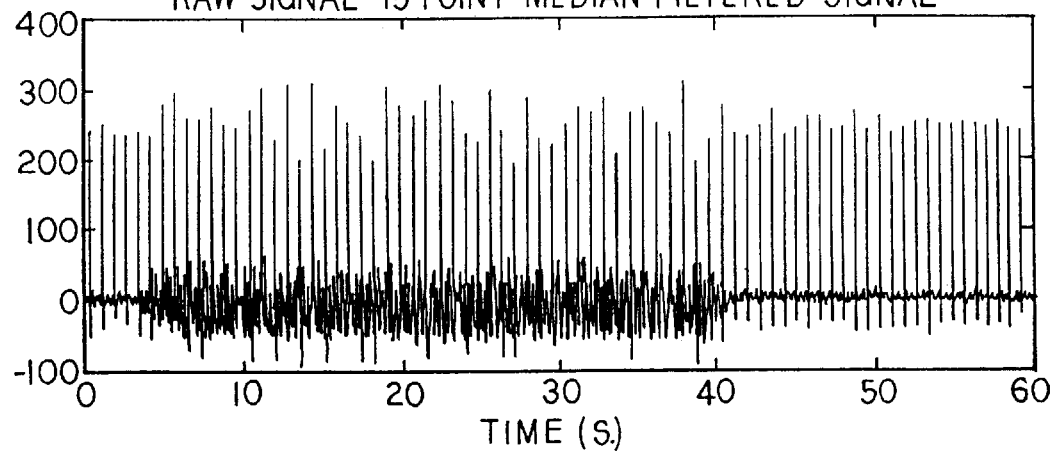
FIG.11B — RAW SIGNAL-15 POINT MEDIAN FILTERED SIGNAL
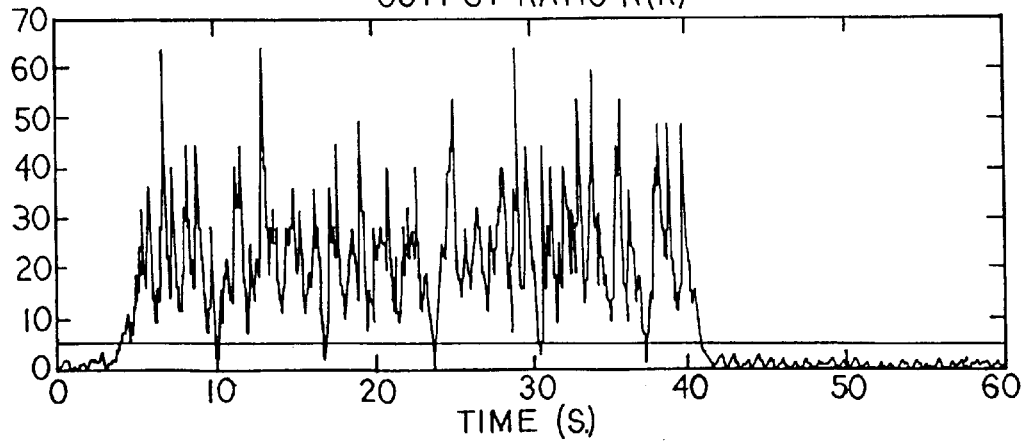
FIG.11C — OUTPUT RATIO R(K)

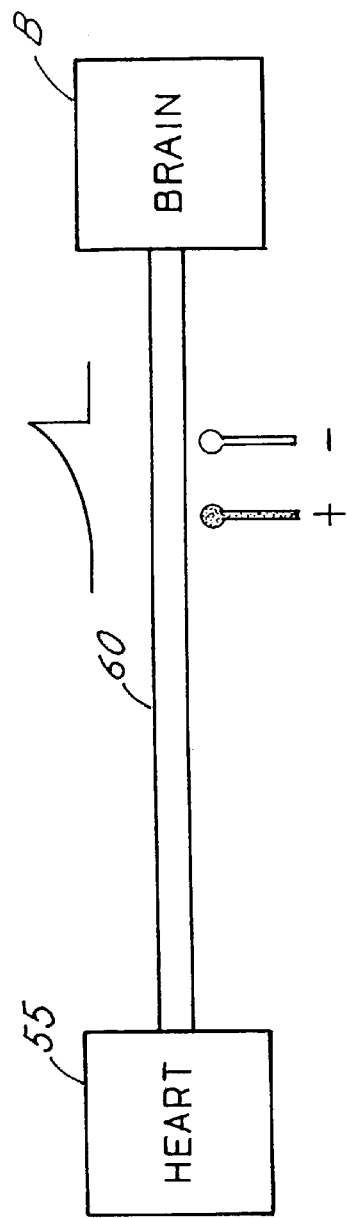
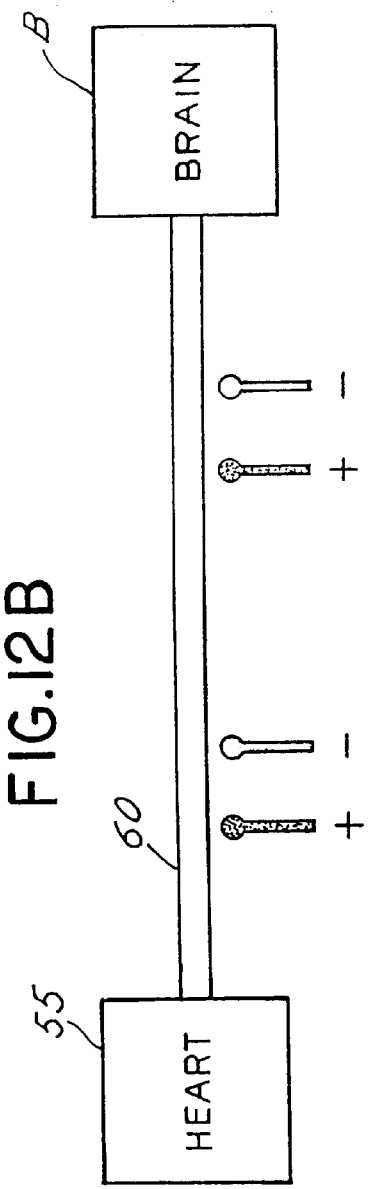

VAGAL NERVE STIMULATION TECHNIQUES FOR TREATMENT OF EPILEPTIC SEIZURES

This patent application is a continuation of U.S. patent application Ser. No. 09/302,516, filed Apr. 30, 1999 now U.S. Pat. No. 6,341,236, for which priority is claimed. This parent application is incorporated herein by reference in its entirety.

FIELD OF THE INVENTION

This invention relates to neural tissue stimulation techniques, and more particularly relates to techniques for providing more effective vagus nerve stimulation and for controlling or preventing epileptic seizures with minimized effect on the heart.

BACKGROUND OF THE INVENTION

Epileptic seizures are the outward manifestation of excessive and/or hypersynchronous abnormal activity of neurons in the cerebral cortex. Many types of seizures occur. The behavioral features of a seizure reflect function of the portion of the cortex where the hyper activity is occurring. Seizures can be generalized and appearing to involve the entire brain simultaneously. Generalized seizures can result in the loss of conscious awareness only and are then called absence seizures (previously referred to as "petit mal"). Alternatively, the generalized seizure may result in a convulsion with tonic-clonic contractions of the muscles ("grand mal" seizure). Some types of seizures, partial seizures, begin in one part of the brain and remain local. The person may remain conscious throughout the seizure. If the person loses awareness, the seizure is referred to as a complex partial seizure.

A number of techniques are known to treat seizures including, for example, drug therapy, drug infusion into the brain, electrical stimulation of the brain, electrical stimulation of the nervous system, and even lesioning of the brain. U.S. Pat. No. 5,713,923 entitled Techniques of Treating Epilepsy by Brain Stimulation and Drug Infusion" generally discloses such techniques in the background section and specifically discloses techniques for drug infusion and/or electrical stimulation to treat epilepsy. This patent is incorporated herein by reference in its entirety.

U.S. Pat. No. 5,025,807 entitled "Neurocybernetic Prosthesis" and its parentage (U.S. Pat. Nos. 4,867,164 and 4,702,254) (all three patents are collectively referred to herein as the "Zabara patents") disclose techniques for electrical stimulation of the vagus nerve. These Zabara patents generally disclose a circuit-based device that is implanted near the axilla of a patient. Electrode leads are passed from the circuit device toward the neck and terminate in an electrode cuff or patch on the vagus nerve.

The neuro-cybernetic prosthesis (NCP) is the primary vagus nerve stimulation (VNS) system that is presently available. This presently available VNS treatment technique for the treatment of epilepsy, however, has limited therapeutic efficacy and exerts clear but variable chronotropic effects on the human heart. See Handforth et. al., "Vagus Nerve Stimulation Therapy for Partial Onset Seizures: A Randomized Active Control Trial," J. Neurology, Vol. 51, pp. 48–55 (1998); Han et al, "Probable Mechanisms of Action of Vagus Nerve Stimulation in Humans with Epilepsy: Is the Heart the Window into the Brain?" AES Proceedings, p. 83 (1997); Frei et al., "Effects of Vagal Stimulation on Human EEG," AES Poceedings, p. 200 (1998) (each of these references are incorporated herein by reference in their entireties). With regard to the heart, vagus nerve stimulation has the side-effect of altering the heart rate. See Frei et al. "Effects of Vagal Stimulation on Human ECG," Abstract from the Annual Meeting of the American Epilepsy Society, Vol. 39, Supp. 6 (1998), which is incorporated herein by reference in its entirety. Typically, activation of the device and stimulation of the vagus nerve causes the heart to experience a significant drop in heart rate. For example, FIG. 1A is graph illustrating the effects of vagus nerve stimulation on the heart rate for a patient. In this Figure, the horizontal axis represents time and the vertical axis represents the normalized heart rate. A value of 1 in this graph indicates that the instantaneous heart rate (IHR) at that point in time is equal to the median IHR for the current vagus nerve stimulator (VNS) device cycle (i.e., for the current 5 ½ minute window). The graph shows that during vagus nerve stimulation from time 0 to 50, the heart rate drops to as low as 0.8 of its background rate. Similarly, FIG. 1B is a graph of the instantaneous heart rates (defined herein) of a patient as a function of time over an 8 hour period. The sharp drops that occur periodically along the bottom of the graphed line correspond to times when the vagus nerve stimulation device is reset or turned "on". These sharp drops illustrate the effect that vagus nerve stimulation has on the heart. Notably, the Zabara patents recognize that the heart rate slows as a result of the stimulation. This effect that vagus nerve stimulation has on the heart is undesirable due to negative short- or long-term effects on the patient. For example, the heart may become less adaptable to stresses due to the vagus nerve stimulation, which may lead to arrhythmia, asystole (heart stoppage), and possibly even to sudden death. See Asconape et al, "Early Experience with Vagus Nerve Stimulation for the Treatment of Epilepsy; Cardiac Complications, AES Proceedings, p. 193 (1998) (incorporated herein by reference in its entirety).

The relative lack of efficacy and the adverse effects of the VNS are attributable in part to inadequate stimulation. Specifically, the NCP does not change the electroencephalogram (EEG) reading. See Salinsky et al. "Vagus Nerve Stimulation Has No Effect on Awage EEG Rythms in Humans," J. Epilespia, Vol. 34 (2), p.299–304 (1993). Adequate stimulation of the vagus nerve induces either synchronization or desynchronization of brain rhythms depending on the stimulation parameters used. See Michael H. Chase et al., "Afferent Vagal Stimulation: Neurographic Correlates of Induced EEG Synchronization and Desynchronization," Brain Research pp. 236–249 (1967); Chase et al, "Cotical and Subcortical Patterns of Response to Afferent Vagul Stimulation," Experimental Neurology, Vol. 16, pp. 36–49 (1966). EEG desynchronization requires selective activation of slow conducting nerve fibers. This state of desynchronization does not favor the occurrence of seizures and is therefore preferred for this specific therapeutic purpose. The absence of EEG changes in humans during VNS suggests stimulation is inadequate and this in turn may explain its relatively low therapeutic value. See Handforth et. al., "Vagus Nerve Stimulation Therapy for Partial Onset Seizures: A Randomized Active Control Trial," J. Neurology, Vol. 51, pp. 48–55 (1998).

In addition, VNS provides non-selective bi-directional nerve fiber activation. In general, the VNS stimulation affects the brain (a desirable target) and also the viscera, including the heart (undesirable targets). Accordingly, VNS causes alterations in the heart electro-cardiogram (EKG) reading. Given the shape of the pulse, its biphasic nature and the intensity settings available in the NCP, selective stimulation of slow conducting nerve fibers (a necessary condition for EEG desynchronization) is highly unlikely with this device.

Further, the NCP provides indiscriminate timing for stimulation of the heart. Cardiac arrest can result from stimulation of the heart during vulnerable phases of its cycle. See Jalife J, Anzelevitch C., "Phase resetting and annihilation of pacemaker activity in cardiac tissue," Science 206:695–697 (1979); Jalife J, Anzelevitch C., "Pacemaker annihilation: diagnostic and therapeutic implications," Am. Heart J. 100:128–130 (1980); and Winfree A T., "Sudden Cardiac Death: A Problem in Topology," Sci Am 248:144–161 (1983). VNS can cause cardiac arrest because the timing of stimulation does not take into account the phase or state of the cardiac cycle.

Accordingly, it is an object of the invention to provide a technique for controlling or preventing epilepsy via stimulation of the vagus nerve with minimized effect on the heart rate. It is another object of the invention to provide a technique for adjusting the vagus nerve stimulation to minimize its affect on the heart rate. It is another object of the invention to provide stimulation of the vagus nerve while maintaining the heart rate at a preset rate. It is a further object to minimize the risk of cardiac arrest in patients receiving VNS by delivering stimuli at times in the heart cycle which cause no or minimal adverse effects on rhythms generation or propagation. Other objects of the present invention will become apparent from the following disclosure.

BRIEF SUMMARY OF THE INVENTION

The present invention discloses techniques for treating epilepsy by providing electrical stimulation of the vagus nerve to induce therapeutic EEG changes with little or no potentially serious or life-threatening side-effects, especially to the heart. Accordingly, the present invention discloses techniques for adjusting the vagus nerve stimulation and/or controlling the heart rate during vagus nerve stimulation to maintain the heart within desired parameters. In a preferred embodiment of the present invention, treatment is carried out by an implantable signal generator, one or more implantable electrodes for electrically stimulating a predetermined stimulation site of the vagus nerve, and a sensor for sensing characteristics of the heart such as heart rate. The heart rate information from the sensor can be used to determine whether the vagus nerve stimulation is adversely affecting the heart. Once threshold parameters are met, the vagus nerve stimulation may be stopped or adjusted. In an alternative embodiment, heart EKG signals may be monitored and applied to an EKG algorithm to detect epileptic seizures and to responsively trigger the signal generator to provide stimulation to the vagus nerve.

In an alternative embodiment, the invention may include a modified pacemaker to maintain the heart in desired conditions during the vagus nerve stimulation. In yet another embodiment, the invention may be simply a modified pacemaker having circuitry that determines whether a vagus nerve is being stimulated. In the event that the vagus nerve is being stimulated, the modified pacemaker may control the heart to maintain it within desired conditions during the vagus nerve stimulation.

In yet another embodiment, EKG rhythms maybe sensed so as to minimize EKG changes via cybernetic techniques. In another embodiment, the present invention may selectively stimulate certain fiber groups within the vagus nerve to block the propagation of impulses towards the viscera, such as the heart, using electrophysiologic techniques. In still another embodiment, the present invention may sense brain EEG to provide feedback on the vagal nerve stimulation. Alternatively, heart EKG may be monitored to determine whether there is a risk of a possible seizure onset to either adjust the VNS stimulation or to warn the patient.

BRIEF DESCRIPTION OF THE DRAWINGS

These and other advantages and features of the invention will become apparent upon reading the following detailed description and referring to the accompanying drawings in which like numbers refer to like parts throughout and in which:

FIG. 1A is graph illustrating the effects of vagus nerve stimulation on the heart rate for a patient.

FIG. 1B is a graph of the instantaneous heart rate of a patient as a function of time over an 8 hour period.

FIG. 3 is a block diagram depicting the connection between the sensor and the signal generator.

FIG. 4 is a schematic block diagram of a microprocessor and related circuitry for utilizing the sensor to control stimulation administered to the vagus nerve.

FIGS. 11A–C are graphs illustrating the EKG signal as it is processed by the algorithm of FIG. 11.

FIGS. 12A–B are schematic diagrams of one or more electrode pairs providing stimulation to the vagus nerve in accordance with an embodiment of the present invention.

DETAILED DESCRIPTION OF THE INVENTION

Figure 2:
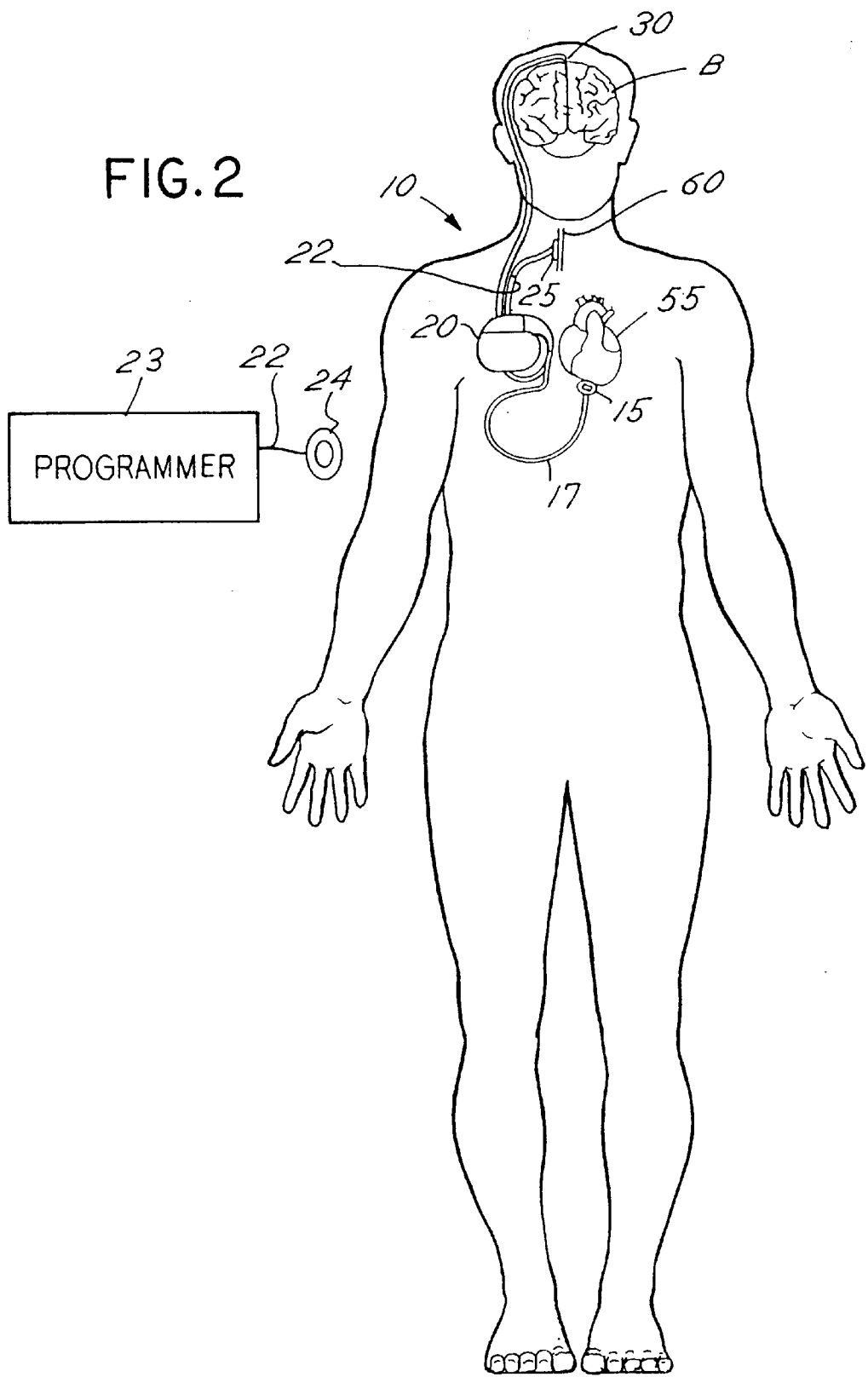
FIG. 2 is a schematic block diagram of the components of the present invention implanted within a patient in accordance with a preferred embodiment of the present invention.

Referring to FIG. 2, a system 10 made in accordance with a preferred embodiment may be implanted below the skin of a patient. System 10 generally includes a sensor 15 for sensing a characteristic of the heart 55 of the patient, a signal generator 20, and one or more stimulation electrodes 25. System 10 may be a modified version of the devices disclosed in the Zabara patents and are incorporated herein by reference.

Sensor 15 is implemented at or near the heart 55 to sense a characteristic of the heart 55, including the heart rate. A number of techniques may be used to sense the heart rate including, but not limited to, QRS detection or R-wave detection techniques, for example, as disclosed in Antti Ruha et al., "A Real-Time Microprocessor QRS Detector System with a 1-ms Timing Accuracy for the Measurement of Ambulatory HRV," IEEE Transactions on Biomedical Engineering, Vol. 44, No. 3, pp. 159–167 (March 1997). Another technique may use standard analog techniques. In alternative embodiments, sensor 15 may be physically located outside of the body and communicate with the implanted portion through telemetry.

Sensor 15 is coupled to signal generator 20 via cable 17. Sensor 15 and signal generator 20 may alternatively communicate via telemetry such as, for example, radiofrequency signals. Alternatively, sensor 15 and signal generator 20 may be a single device that may be part of a heart pacemaking or like device. Depending upon the sensor 15 used, the outputs of sensor 15 may require the use of an analog-to-digital (A/D) converter 18 to be coupled between sensor 15 and signal generator 20 as shown in FIG. 3. The output of A/D converter 18 is connected to microprocessor 200 as shown in FIG. 4. Alternatively, if an A/D converter 18 is not required, the output from sensor 15 can be filtered by an appropriate electronic filter 19 prior to delivery of the sensor signal to signal generator 20.

When in operation to stimulate the vagus nerve 60, signal generator 20 receives the sensed information from sensor 15 and adjusts the stimulation therapy in response to the sensed information in accordance with the present invention. Signal generator 20 is preferably capable of providing a range of stimulation therapy with adjustable cycling parameters of the electrical pulse including but not limited to pulse shape, inter-stimulus interval, pulse frequency, pulse width, pulse amplitude, and pulse phase. As discussed herein, it is preferred that the stimulation be accomplished so as to have minimal effect on the heart. Continuous stimulation may also be provided. Preferably, signal generator 20 is of the type which is capable of ramping up to the set pulsing parameters whenever the signal generator 20 is activated. This technique helps eliminate involuntary twitching when the prosthesis is activated. Once implanted, signal generator 20 must be "tuned" to provide desired treatment therapy to the specified nerve properties of the vagus nerve 60. Signal generator 20 accordingly is capable of varying before and after implant the pulsing parameters of the pulse signal. After implant, the pulsing parameters may be adjustable via telemetry which is known to those skilled in the art.

As shown in FIG. 3, signal generator 20 may include a microprocessor 200 that is coupled to the output of A/D converter 18, filter 19 or directly to sensor 15. Microprocessor 200 processes the sensor data in different ways depending on the type of transducer in use. Microprocessor 200 may read the sensor signal and stores one or more values in RAM 102a. Referring now to FIG. 4, memory 204 may be used to store parameters for control of the stimulation therapy based on the sensor signal. Microprocessor 200 is coupled to a peripheral bus 202 having address, data and control lines. Stimulation is delivered through an output driver 224.

Signal generator 20 is suited to provided stimulation therapy with adjustable pulse frequency, pulse width and pulse amplitude. The stimulus pulse frequency is controlled by programming a value to a programmable frequency generator 208 using bus 202. The programmable frequency generator 208 provides an interrupt signal to microprocessor 200 through an interrupt line 210 when each stimulus pulse is to be generated. The frequency generator 208 may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude. Microprocessor 200 also programs a pulse width control module 214 using bus 202. The pulse width control provides an enabling pulse of duration equal to the pulse width via a conductor 216. Pulses with the selected characteristics are then delivered from signal generator 20 through cable 22 to the electrodes 25 which are in communication with the vagus nerve 60. Electrical stimulation of the vagal nerve 60 maybe implemented by providing pulses to electrodes 25 having amplitudes of 0.1 to 20 volts, pulse widths varying from 0.02 to 1.5 milliseconds, and repetition rates varying from 2 to 2500 Hz. The appropriate stimulation pulses are generated by signal generator 20 based on the computer algorithm, parameters set by the clinician, and the features of the present invention.

Microprocessor 200 executes an algorithm to provide stimulation with closed loop feedback control based on the sensed conditions of the heart from sensor 15. At the time the signal generator 20 is implanted, the clinician programs certain key parameters into the memory of the implanted device via telemetry. These parameters may be updated subsequently as needed. Alternatively, the clinician may elect to use default values. The clinician must program the range of values for pulse width, amplitude and frequency which signal generator 20 may use to optimize the therapy.

The stimulation may be applied continuously to prophylactically prevent the onset of seizures, manually by the patient, or it may turn on in response to a signal on secondary sensor 30 (discussed herein) indicating the beginning of a seizure. Stimulus parameters can be adjusted by the computer algorithm within a range specified by the clinician in an attempt to optimize the seizure suppression.

Signal generator 20 is implanted in a human body in a subclavicular, subcutaneous pocket. Signal generator 20 may also be implanted near the heart 55. For example, in one embodiment discussed herein, signal generator 20 may be encased along with sensor 15 near the heart 55. Signal generator 20 may take the form of a modified neurocybernetic prosthesis (NCP) device, a modified signal generator Model 7424 manufactured by Medtronic, Inc. under the trademark Itrel II, or any other signal generator suited for stimulation of the vagus nerve 60. Signal generator 20 may also be similar to one disclosed in the Zabara patents, which are incorporated herein by reference, with the modification that it be adjustable and responsive to sensor 15.

Signal generator 20 is coupled to the proximal end of at least one lead 22. The distal end of 22 terminates in one or more stimulation electrodes 25 that can stimulate neurons in the vagus nerve 60. The electrodes 25 are shown as an electrode patch, which is generally known in the art, though single electrodes may also be used. Various other known electrodes may also be used such as, for example, a tripolar cuff electrode. The electrodes 25 maybe of the form disclosed in the Zabara patents and are incorporated herein by reference. Electrode patches include both positive and negative electrodes. Electrodes 25 may be placed anywhere along the length of the vagus nerve 60, above or below the inferior cardiac nerve depending upon the particular application. Electrodes 25 are placed on or near the vagus nerve 60 or in indirect contact with the vagus nerve 60.

FIG. 12A shows an embodiment of the present invention having a pair of electrodes for use in different combinations. The electrode pair is positioned to stimulate the vagus nerve 60. As preferred, the anode is implanted to be closest to the heart so as to block passage of unwanted nerve impulses towards the viscera, such as the heart. The pulse is preferably a saw-tooth wave as shown as having a steeply rising beginning followed by a slow exponential decay, although any other way may be used. The outward flow of current at the cathode, triggers conducted impulses in larger and smaller nerve fibers while the inward inflow at the anode inactivates the conduction of impulses in the smaller or slower conduction fibers. The differential effect of anodal currents results form the greater internal conductances and greater conduction velocity of larger (faster) conducting nerve fibers. See Accornero et al. "Selective Activation of Peripheral Nerve Fibre Groups of Different Diameter by Triangular Shaped Pulses," J. Physiol., pp. 539–560 (1977). Simply stated, anodal currents causes a functional nerve block.

Alternatively, a modification of the above technique may be implemented which rests on the Alaw of independent conduction@ of nerve fibers. Bures et al., "Electrophysiological Methods in Biological Research," Academic Press New York, London, pp 338–339 (3rd ed. 1967). This law generally states that larger fibers will conduct impulses faster than smaller fibers. In this embodiment, impulses travelling in larger or myelinated fibers will reach the anode well before the smaller or slower conducting fibers and while the functional block is still active. See Jones et al., "Heart rate responses to selective stimulation of cardiac vagal C fibers in anaesthetized cats, rats and rabbits," J. Physiol (London) 489.1:203–214 (1995). These fast impulses which are more likely to alter the heart than the slow conducting ones, will be prevented from reaching the heart (Id.). The distance between the active electrodes should be sufficiently long so as to allow the differential conduction of impulses to fully take place or develop. The optimal distance between these electrodes can be found during the implantation procedure.

If the anodal current is maintained for a sufficiently long period of time, the slow traveling impulses can be also blocked from reaching the heart. The duration of anodal stimulation necessary to attain this effect can be determined during the implantation procedure or at a later time. Those skilled in the art understand that more than one pair of electrodes and different impulse shapes, phases and time constants may be used to optimize blockage of impulses travelling towards the heart using collision techniques. See Jones et al., "Heart rate responses to selective stimulation of cardiac vagal C fibers in anaesthetized cats, rats and rabbits," J Physiol (London) 489.1:203–214 (1995). Electrodes can be used not only to transfer energy to the vagus nerve 60 but also to record its activity.

FIG. 12B discloses that two more electrode pairs may also be used with the pair closest to the heart serving to guard against fast conducting fibers that may pass through to the heart. Again, each of the paired electrodes are configured so that the anode is closest to the heart. See Jones et al., "Heart rate responses to selective stimulation of cardiac vagal C fibers in anaesthetized cats, rats and rabbits," J Physiol (London) 489.1:203–214 (1995). The use of asymmetric shielded two or single electrode cuffs is described in U.S. Pat. Nos. 4,628,942 and 4,649,936, which are incorporated herein by references in their entireties. These electrodes were designed to allow unidirectional spread and will be placed around the vagus nerve 60 in a manner which will ensure that impulses during stimulation will travel only in the direction of the brain, ensuring maximal efficacy and minimal cardiac side effects.

As another option, high frequency (>100 Hz) stimulation of a portion of the nerve proximal to the heart may be implemented to prevent the treatment stimulation from affecting the heart. This is desirable since high frequency stimulation causes a functional block of the part of the nerve under stimulation.

It is optionally desirable to provide selective stimulation of the vagus nerve 60 based on fiber types and using various pulsing techniques to achieve unidirectional activation of action potentials. The fiber types of the vagus nerve 60 may be selected in accordance with the techniques disclosed in U.S. Pat. Nos. 4,628,942 entitled "Asymmetric Shielded Two Electrode Cuff"; U.S. Pat. No. 4,649,936 entitled "Asymmetric Single Electrode Cuff for Generation Of Unidirectionally Propagating Action Potentials For Collision Blocking"; and Accornero et al. "Selective Activation of Peripheral Nerve Fibre Groups of Different Diameter by Triangular Shaped Pulses," J. Physiol., pp. 539–560 (1977) all of which are incorporated herein in their entireties. This will allow the effects of the stimulation to reach the brain as desired while minimizing the effects of the stimulation on the heart.

System 10 may include additional components including for example a second sensor 30 implanted within the brain that provides closed-loop feedback of sensed conditions indicative of a possible seizure onset. Second sensor 30 may be coupled to signal generator 20 in a manner similar to that depicted in FIG. 3. The Zabara patents disclose such closed-loop feedback systems and are incorporated herein by reference. U.S. Pat. No. 5,713,923 entitled "Techniques of Treating Epilepsy by Brain Stimulation and Drug Infusion" ("the '923 patent") also discloses such techniques for closed-loop feedback control and the types of sensors that can be used. The '923 patent is incorporated herein by reference in its entirety. System 10 may also be implemented as an open-loop system where the patient may manually operate a switch to turn "on" and "off" the vagus nerve stimulation system 10 based on sensed aura indicative of a seizure onset. Even with a fully implanted device, a momentary contact switch, a magnetically operated reed switch, or a number of other devices may be utilized to provide external control of the implanted device. Those skilled in the art will appreciate how to implement such devices.

Figure 5:
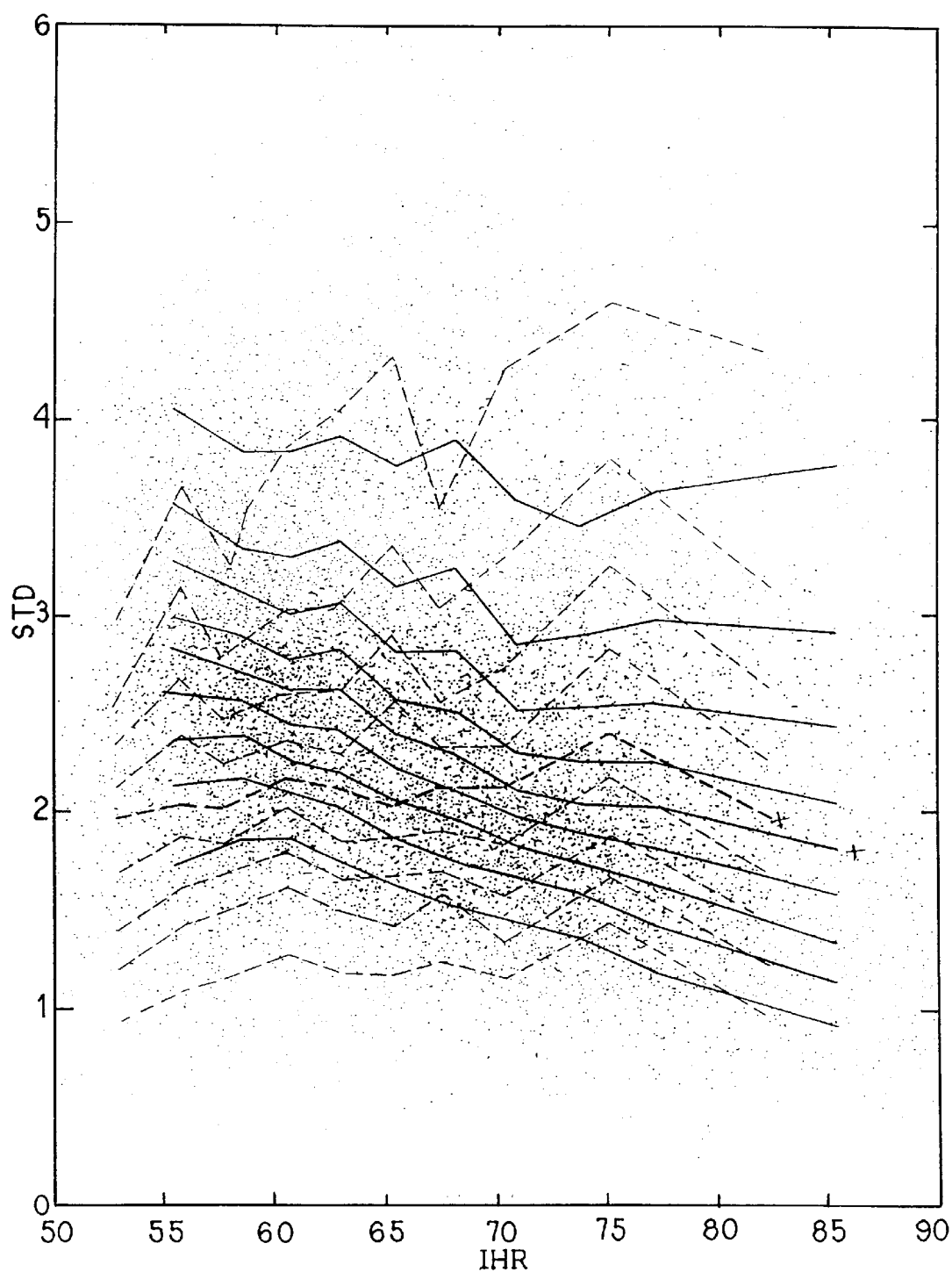
FIG. 5 is a graph of standard deviations of the instantaneous heart rate (IHR) of a patient as a function of the IHR.

It is an object of the present invention to minimize or eliminate the effects on the heart caused by the electrical stimulation of the vagus nerve 60. The techniques for achieving this are discussed herein, but reference to FIG. 5 is made for a more defined understanding of the problem. FIG. 5 is a graph of standard deviations (SDT) of the instantaneous heart rate (IHR) of a heart of a patient as a function of the IHR. The IHR is number of beats of the heart per minute at any given time. IHR may be calculated by first measuring (in seconds) the time between two beats of the heart to derive the pulse rate or the beat interval. IHR is then determined by dividing 60 by the beat interval.

Referring still to FIG. 5, the horizontal axis is the instantaneous heart rate (IHR) averaged for 5 consecutive beats and the vertical axis is the standard deviation of the IHR measurements for the same 5 beats. The dots or points on the graph represent the standard deviations of the IHR measurements as a function of the IHR during the time period when the vagus nerve stimulator (VNS) is off. The solid lines in the graph represent 10 percentile divisions with the darkest solid line being the median standard deviation as a function of the IHR. As shown in the graph of FIG. 5, there is an inverse proportion between the IHR and the standard deviation, namely at lower IHR there is greater variability of the heart rate (higher standard deviation between IHRs) and as the heart beats faster (higher IHR) there is less variability of the heart rate (lower standard deviation between IHRS). However, when the vagus nerve 60 is electrically stimulated, this relationship changes as depicted by the dashed lines in the graph (darkest dashed line being the median standard deviation as a function of the instantaneous heart rate). The inventors have found that the relationship between the IHR and the standard deviation between the IHRs is altered by electrical stimulation of the vagus nerve 60. Generally, stimulation of the vagus nerve 60 increases heart rate variability (standard deviation) at higher IHR values. It is therefore desirable to provide a technique for vagus nerve stimulation that minimizes or has no effect on the normal operation of the heart as measured by the standard deviation of the IHR as a function of the IHR.

Vagus nerve stimulation may be adjusted or controlled based on instantaneous heart rate (IHR) measurements and/or heart rate variability. Those skilled in the art will recognize that other measures of cardiac cycle lengths may alternatively be used besides IHR. The following control algorithm, with reference to FIG. 6, may be utilized to minimize the effect of vagus nerve stimulation on the heart. At step 605, sensor 15 can measure the pulse rate or beat interval in seconds. The beat interval is generally the time period between heart beats. At step 610, the instantaneous heart rate (IHR) is calculated, by dividing 60 by the beat interval (i.e., 60/beat interval). At step 615, heart rate variability can optionally be measured depending upon how the feedback is to be accomplished (discussed herein in further detail). Heart rate variability can be based on the IHR calculation using any number of techniques. A number of known systems exist for determining heart rate variability, including by way of example, that disclosed in U.S. Pat. No. 5,330,508 which is incorporated herein by reference. However, these known are generally inapplicable as they require heart rate variability measurements over long intervals of time, typically 5 minutes. As preferred, the present invention measures heart rate variability based on much short time periods of IHR measurements, preferably 3 to 5 beat intervals. Those skilled in the art will appreciate that longer periods may be used to practice the invention. Heart rate variability may, for example, be taken by calculation of the standard deviation of 5 IHR measurements (as illustrated in FIG. 5 discussed above). Another way to measure heart rate variability is to establish a statistical analysis of the heart rate variabilities based on past IHR measurements. Those skilled in the art will appreciate that any number of techniques maybe employed to measure heart rate variability based on relatively shorter periods of time.

Figure 6:
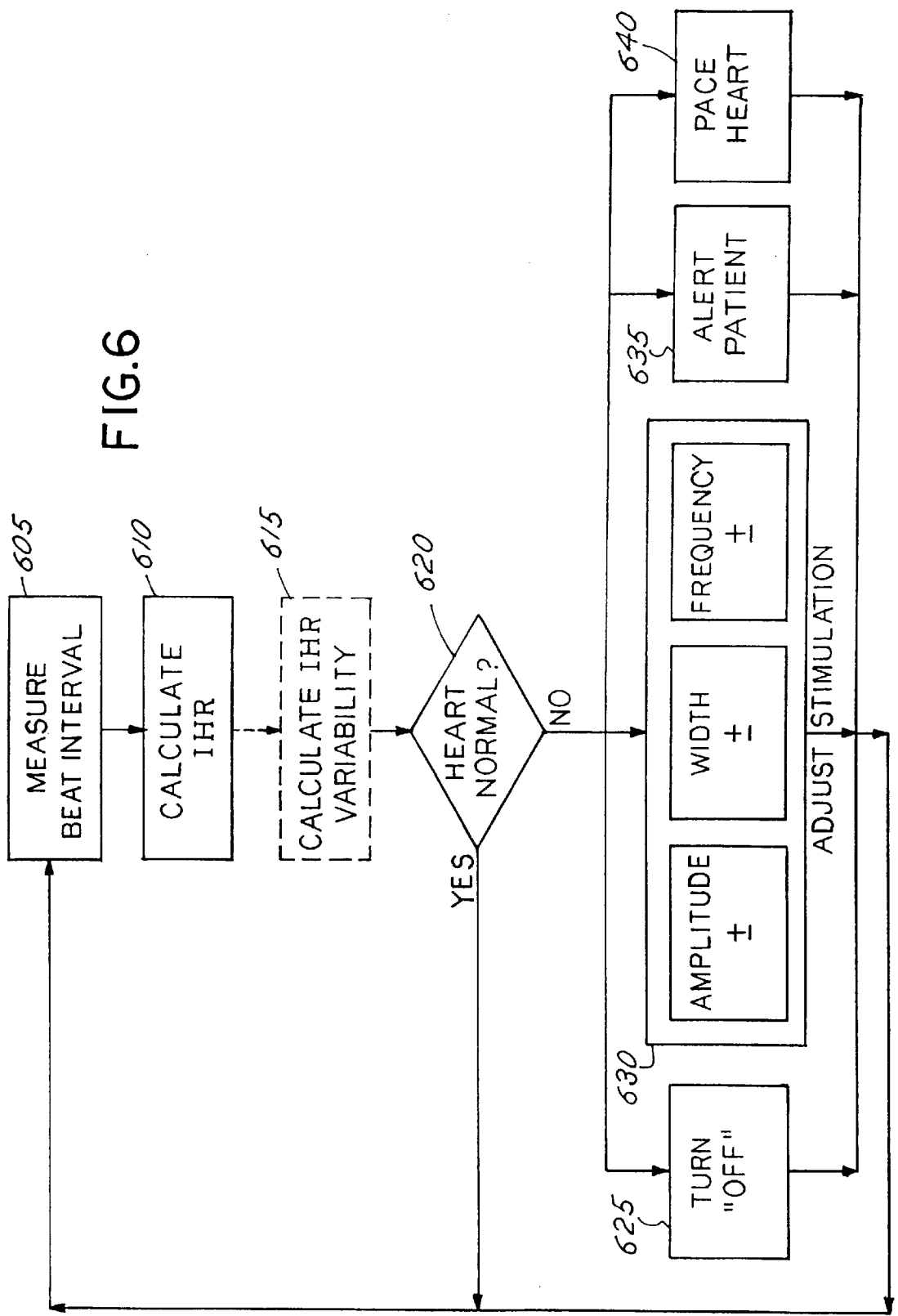
FIG. 6 is a flow chart depicting a control algorithm utilized to minimize the effect of vagus nerve stimulation on the heart.

Referring still to control algorithm of FIG. 6, once the heart rate variability is determined, the system monitors, at step 620, whether the heart is operating within its normal parameters as illustrated in FIG. 5 by the solid lines in the graph. If it is determined that heart rate variability is too high or too low relative to the IHR for that time period, the stimulation of the vagus nerve 60 is adjusted to bring the heart into its normal heart rate variability parameters. If the heart rate and/or heart rate variability are maintained within their normal patterns, then no changes to the stimulation are made.

The determination of step 620 can be made in any number of ways. It may be made based on IHR measurements, or heart rate variability measurements, or both. For example, if more than a 10% change occurs in the median IHR rate between the "off" and "on" segments, then an adjustment to the vagus nerve stimulation should be made. As another example, if the summed standard deviation values for 3–5 consecutive IHR measurements exceeds a certain number, then the stimulation of the vagus nerve 60 needs to the adjusted. So if the standard deviation is measured to be at least 4 at the IHR of 80 (being above the 90th percentile four times in a row) for 3 consecutive IHR measurements, then it is clear that the heart rate variability is not normal and the vagus nerve stimulation needs to be adjusted or simply turned off. Those skilled in the art will appreciate that any number of criterion such as these may be established to determine when the heart is not operating in its normal fashion. The system 10 may monitor variability so that it is not too high or even too low. In addition, the system 10 may have memory for a learning capability such that it can learn the heart rate variability characteristics during normal operation of the specific patient's individual heart and the decision-making criterion of step 620 may be adjusted accordingly. Further, the physician may adjust the parameters for when the vagus nerve stimulation needs to be adjusted to account for the specific needs of each individual patient.

At step 625, if it is determined that the vagus nerve stimulation needs to be adjusted, any number of approaches may be taken. One option is that the patient may be alerted by an audio signal or beep to manually turn off the stimulation device. The audio signal may alternatively be a stimulation device that provides sensory stimulation, or a vibrating mechanism similar to a pager. Another option is to automatically turn off the stimulation provided to the vagus nerve 60. A third option is to adjust the stimulation by adjusting the pulse frequency, amplitude, and/or width (discussed further herein). A fourth option is to provide signaling to a pacemaker to maintain the heart rate at a desired level (discussed further herein).

In the event that it is determined that the heart rate variability is too low, then stimulation can be altered to increase variability. Similarly, if the variability is too high, stimulation can be altered to decrease variability. The VNS may be set to provide a stimulation cycle. It is desirable to utilize the law of independent conduction, discussed above, when providing the electrical stimulation. In particular, depending upon the parameters to be used, can stimulate different fiber widths.

As discussed above, specifically targeting certain tissue types within the VNS can be beneficial in minimizing the side-effects of the VNS. As such, the VNS may be set to stimulate selectively slow conducting vagal nerve fibers using appropriate stimulation parameters which include but are not limited to delivering saw-tooth shape anodal pulses. Selection of parameters such as time of exponential decay, frequency of stimulation, length of stimulation, interstimulus interval, etc. can then be optimized for each individual.

Figure 7:
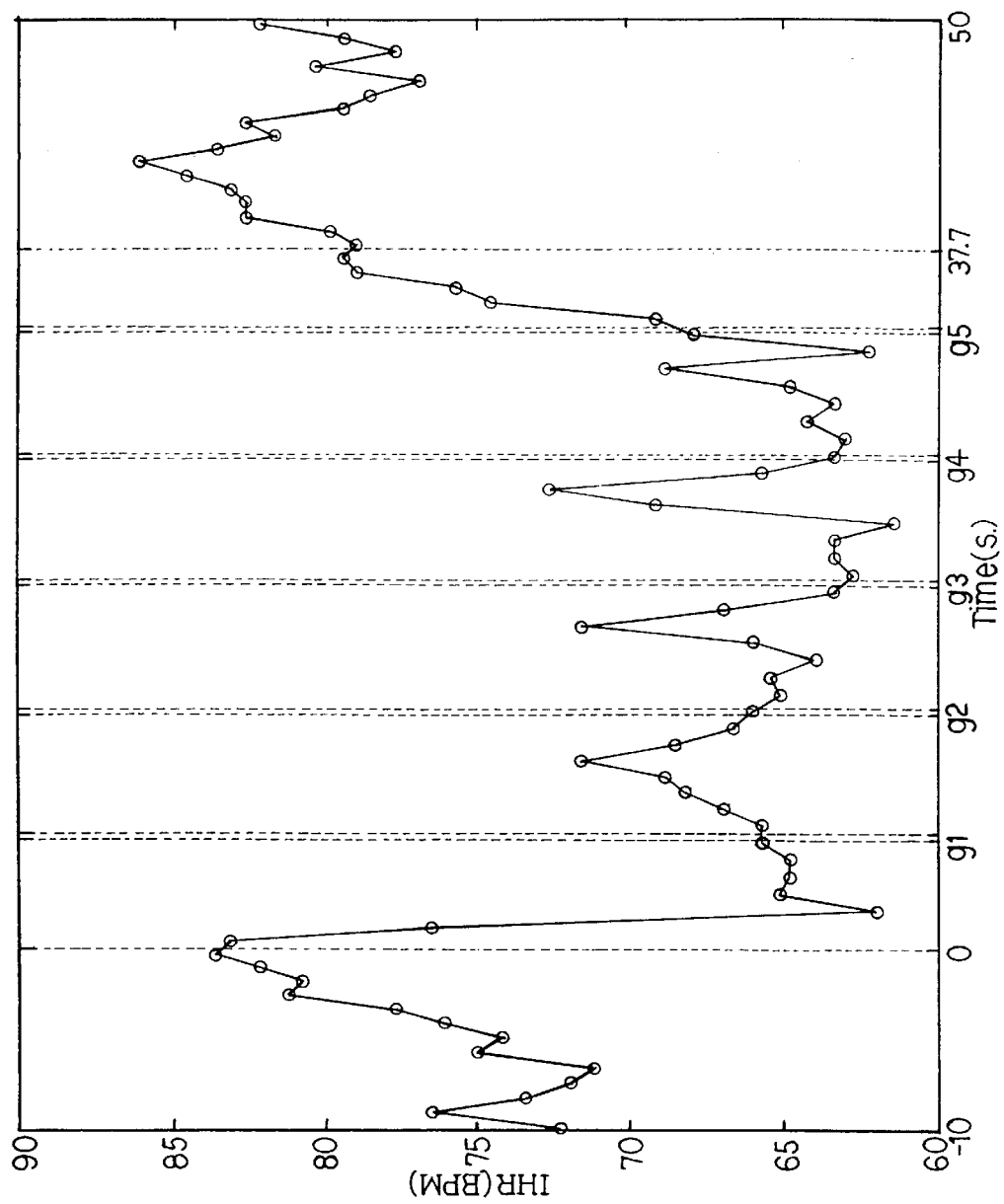
FIG. 7 is a graph depicting the IHR of a patient as a function of time.

Another possibility to achieve the desired heart rate or heart rate variability is to make use of certain periods of time when the VNS is "off". Referring to FIG. 7, a chart is shown of the IHR of a patient as a function of time. Time period 0 through 37.7 reflects the period during which the VNS is turned "on". The time periods g1 through g5 reflect time periods when the stimulator resets itself and no stimulation is delivered to the vagus nerve 60. Thus, though these "off gaps" are due to certain aspects of the VNS and are therefore undesirable, they may be useful to achieve the desired heart rate or heart rate variability.

Figure 8:
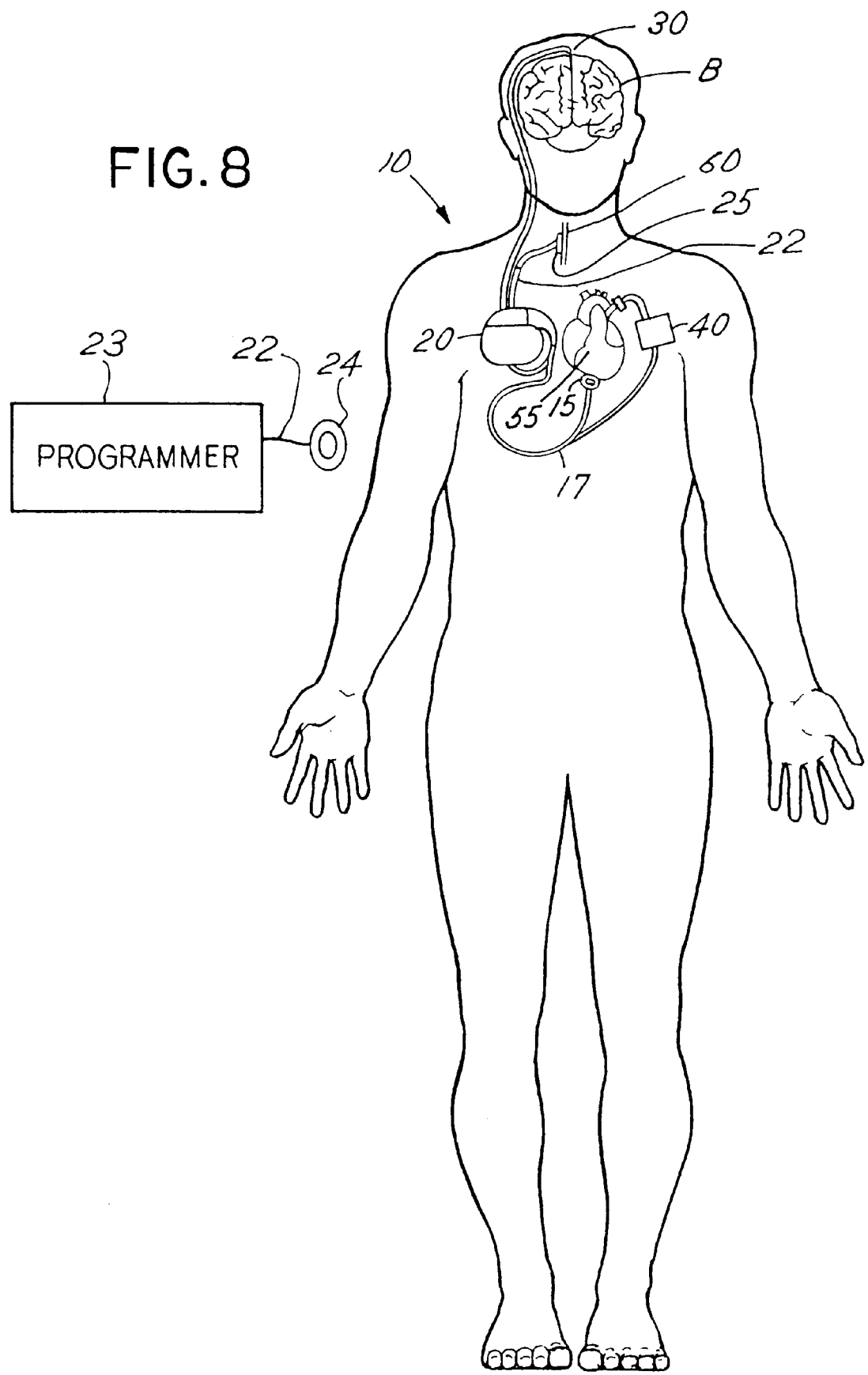
FIG. 8 depicts another embodiment of the present invention having a pacemaker or a like device implemented to affect the heart in the event that vagus nerve stimulation causes the heart to beat outside of the acceptable ranges.

FIG. 8 depicts another embodiment of the present invention having a pacemaker 40 or like device implemented to affect the heart 55 in the event that vagus nerve 60 stimulation causes the heart 55 to beat outside of the acceptable ranges. The pacemaker 40 may control the heart rate and/or may be variable for a period of time during which the vagus nerve 60 is being stimulated. As such, pacemaker 40 is coupled via a lead or telemetry to signal generator 20. The pacemaking parameters may be preset and adjustable by the physician and further adjustable so that the pacemaker 40 maintains heart rate parameters that existed just before the vagus nerve stimulation device was turned "on". Pacemaker may include a processing circuit similar to that of FIGS. 3 and 4 to provide variable pacing of the heart and for processing of any sensor signal. This embodiment may be preferred in the event that the adjustment of the vagus nerve stimulation (embodiment discussed above) reduces the efficacy of avoiding the onset of a seizure. In this regard, the present invention may be incorporated for example within rate responsive pacemakers as disclosed in U.S. Pat. Nos. 5,052,388 and 5,562,711 and commercially available pacemakers sold by Medtronic, Inc. under the trademarks KAPPA® and LEGEND ELITE®. These patents and pacemakers are incorporated herein by reference in their entireties.

In another embodiment, both of the above embodiments are combined such that adjustments are made to the vagus nerve stimulation parameters and also the pacemaker 40 to maintain the heart within a desired rate and variability. The signal generator 20 and pacemaker 40 may be packaged in a single implantable casing, may be coupled via a cable, or may communicate via telemetry.

Figure 9:
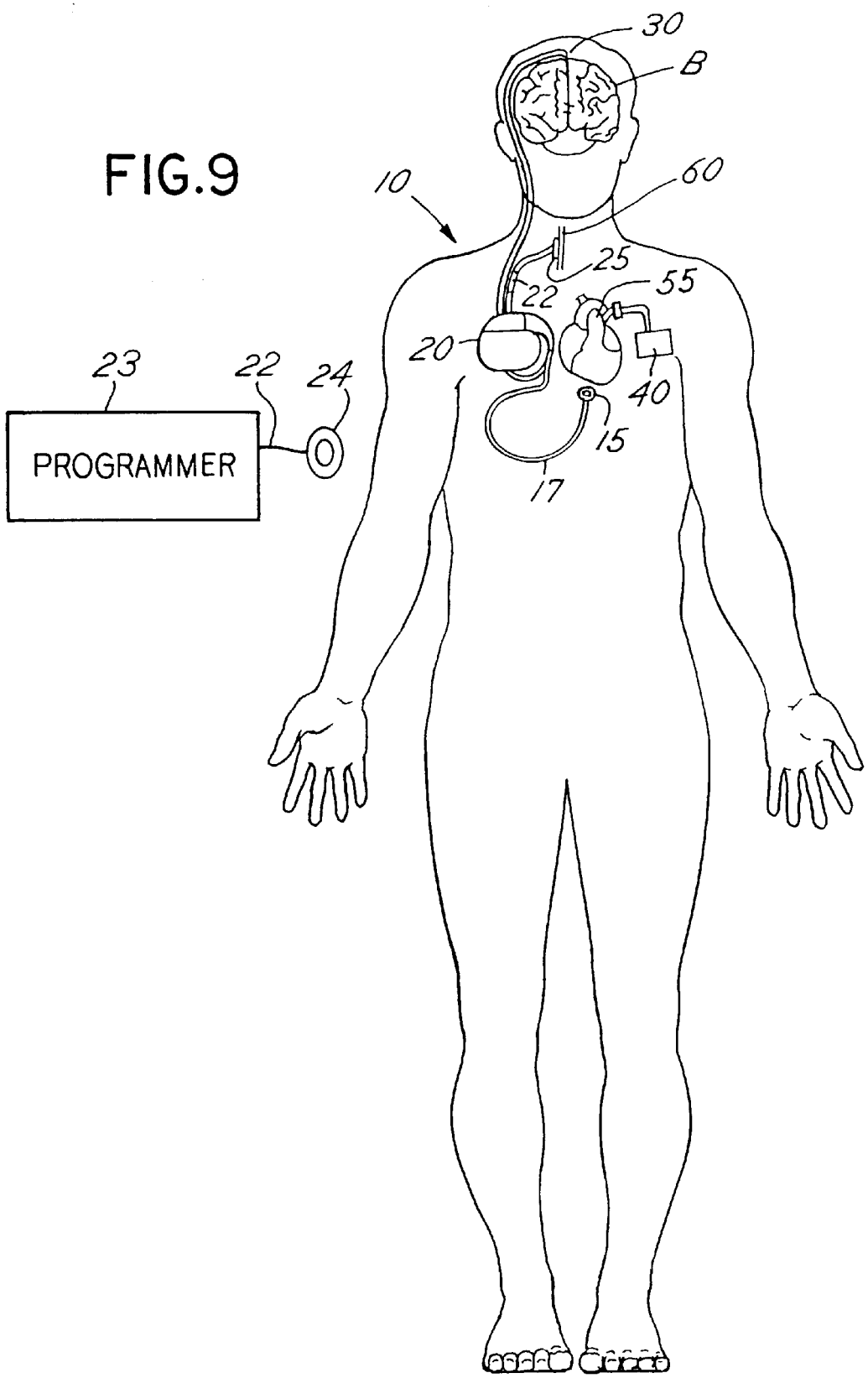
FIG. 9 is a schematic diagram of yet another embodiment of the invention where a pacemaker is modified with a digital signal processing algorithm to recognize whether the vagus nerve is being stimulated.
Figure 10:
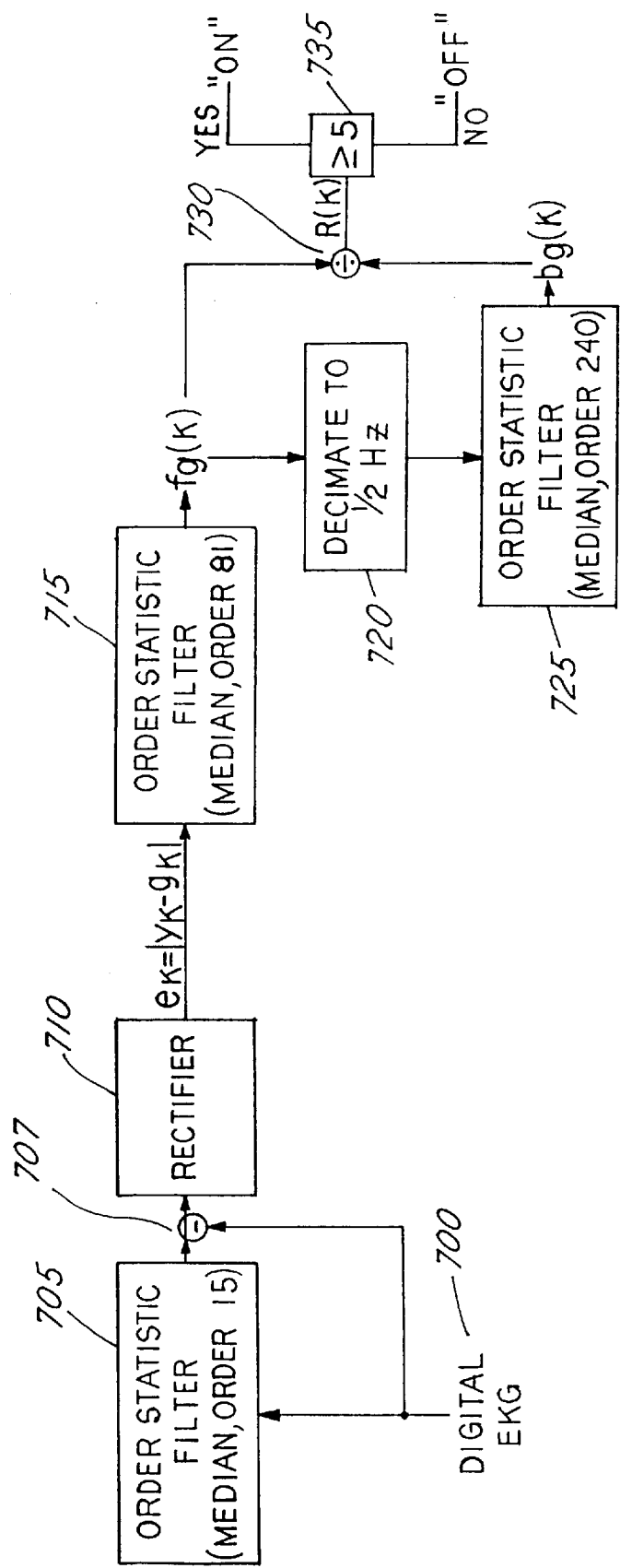
FIG. 10 is a block diagram of an algorithm for detecting whether a vagus nerve stimulator is stimulating the nerve based on heart EKG.

FIG. 9 discloses yet another embodiment of the invention where a pacemaker is equipped with a digital signal processing algorithm to recognize whether the vagus nerve 60 is being stimulated. The pacemaker may provide the necessary pacing of the heart in the event that the algorithm senses that the vagus nerve 60 is being stimulated, shown below. The pacemaker may also serve to maintain the heart rate at safe levels in the event that the patient does experience an epileptic seizure. FIG. 10 is a block diagram of an exemplary algorithm for detecting VNS-induced artifact in the EKG signal to determine when the device is performing vagal nerve stimulation. At 700, the analog EKG signal is digitized (preferably with 240 Hz sampling and 10 bits of precision). At 705, the digital EKG signal (y(k), k=1,2,3, ... ) is then passed into a first order statistic filter (preferably a median filter of order 0.0625 seconds, i.e., 15 data points at 240 Hz sampling rate). At 707, the input to and output from this filter are then adjusted for any filter-induced phase lag and the difference is computed and rectified using the absolute value. Specifically, a signal represented by the following formula is computed at each point in time:

$$e(k)=|y(k)-\text{median }(y(k-7), y(k-6), y(k-5), \ldots, y(k), y(k+1), y(k+2), \ldots, y(k+7))|,$$

for k=8, 9, 10, ... At 715, the e(k) sequence is then passed into a second order statistic filter (preferably of order ⅓ second, i.e., 81 data points at 240 Hz sampling rate). The output of this filter is denoted as fg(k) and is referred to as the foreground sequence. At 720, this output is sampled every 2 second (i.e. decimated by a factor of 120) and at 725 passed through a third order statistic filter of order 2 minutes (i.e., of order 240) to produce a moving background sequence, bg(k). This background sequence is held constant between updates and, at 730, the ratio R(k)=fg(k)/bg(k) is computed for each point in time (every 1/240th of a second). At 735, this ratio sequence is compared against a threshold value (preferably about 5), and the system determines that the stimulation is "on" when R(k). 5 and "off" when R(k)<5. FIG. 11A is a graph showing a raw EKG signal with the VNS artifact on the left side. FIG. 11B is another graph showing the difference between the raw signal and the output of the first median filter 705. FIG. 11C is another graph showing the output ratio R(k) (from the divider 730) and the threshold of 5 to determine when the device is "on" or "off". As can be seen in this graph, the VNS is "on" at roughly time t=5 seconds through t=41 seconds. Known periodicities of the VNS device can be compared with the detected on times to verify whether the VNS is operating in accordance with a desired schedule and stimulation parameters. Accordingly, under this embodiment, the present invention may be implemented to modify a pacemaker that can be used with existing VNS devices or with VNS devices of the present invention.

In another embodiment of the present invention, vagus nerve stimulation may be provided during periods when heart is not vulnerable to stoppage. This can be achieved by sending single pulses and measuring the phase resetting effect on the heart EKG. This will enable us to identify the phase that has the least effect on the heart. Thus, the signal generator 20 may be programmed to trigger only when the cardiac cycle is less vulnerable to stoppage or the part of the cycle when the stimulation has the lowest effect on the heart. This testing can be done by physician in clinic during or after implant or it may be programmed to automatically perform within the signal generator 20. See Jalife J, Anzelevitch C., "Phase resetting and annihilation of pacemaker activity in cardiac tissue," Science 206:695–697 (1979); Jalife J, Antzelevitch C., "Pacemaker annihilation: diagnostic and therapeutic implications," Am Heart J 100:128–130 (1980); and Winfree AT., "Sudden cardiac death: A problem in topology," Sci Am 248:144–161 (1983).

In yet another embodiment of the present invention, vagus nerve stimulation is provided to enhance desynchronization of the EEG rhythms. Desynchronization of EEG (i.e., to achieve an EEG that has relatively low amplitude and relatively high frequency) reduces the probability of seizure occurrence. Accordingly, it is desirable to find the parameters of the VNS stimulation that will optimize the EEG desynchronization. Referring again to FIG. 2, EEG electrode 30 may provide feedback to signal generator 20 so that it can responsively alter the stimulation pulse parameters to induce an EEG having a generally low amplitude and high frequency. Since the EEG characteristics of each patient may vary, testing may be done on the patient of varying stimulation pulses to observe the effects on the EEG. In addition to performing this during implant, this can also be performed periodically or when the patient is sleeping.

In another embodiment of the present invention, the heart may be monitored for real-time changes in EKG for the detection of seizures and automated triggering of VNS. Seizures originating from or spreading to brain areas involved in cardiovascular regulation, cause changes in heart rate, R—R variability and blood pressure. The heart can thereby by monitored for these changes that are indicative of the occurrence of a seizure. Specifically, the changes in the heart rate that may indicate a possible onset of a seizure include non-exertional increases in heart rate, decreases in heart rate, increases in R—R variability, decreases in R—R variability, etc. These patterns may also be learned over time as the patient experiences seizures, the sensor Automated detection of these changes in accordance with the present invention can be also used to turn on the VNS, if it is safe to do so. If the EKG changes occurring during seizures are considered dangerous, the VNS may be turned off or modified to minimize the risk of an adverse reaction. Further, this EKG algorithm can also be used to warn the patient or those around the patient that of abnormal heart function so that the patient may act accordingly to minimize the risk of sudden unexpected death which is common among persons with intractable epilepsy. Accordingly, heart EKG may be monitored by a signal generator system and/or a pacemaker system and may be incorporated within those embodiments of FIGS. 2, 8 and 9.

By using the foregoing techniques for electrical stimulation of the vagus nerve 60, epilepsy can be controlled or prevented with minimized effects on the heart. Those skilled in that art will recognize that the preferred embodiments may be altered or amended without departing from the true spirit and scope of the invention, as defined in the accompanying claims.

We claim:

1. A method of controlling or preventing epileptic seizures comprising the steps of:
    (a) implanting a signal generator in a body;
    (b) implanting at least one electrode to be in communication with a vagus nerve of said body;
    (c) coupling at least one electrode to said signal generator;
    (d) operating the signal generator to provide stimulation pulses to the vagus nerve via the at least one electrode;
    (e) generating a sensor signal indicative of a characteristic of a heart; and
    (f) regulating said stimulation pulses in response to said sensor signal, whereby epilepsy is treated.

2. A method, as claimed in claim 1, wherein said step of regulating comprises the step of executing a control algorithm.

3. A method as claimed in claim 1, wherein said step of generating a sensor signal provides instantaneous heart rate information.

4. A method as claimed in claim 1, wherein said step of generating a sensor signal provides heart rate variability information.

5. A method as claimed in claim 1, wherein said step of implanting the at least one electrode include the step of positioning the at least one electrode to selectively stimulate slow conducting vagus nerve fibers.

6. A method as claimed in claim 1, wherein the step of regulating includes the step of adjusting at least one characteristic of the stimulation pulses, wherein the characteristic is selected from the group consisting of pulse shape, inter-stimulus interval, pulse frequency, pulse width, pulse amplitude, and pulse phase.

7. A method as claimed in claim 1, wherein the step of operating the signal generator is performed in response to a sensing of a possible onset of a seizure.

8. A method as claimed in claim 1, wherein the step of operating the signal generator is performed in response to a user operating a switch to activate the signal generator.

9. A system for controlling or preventing epileptic seizures comprising in combination:
    (a) an implantable signal generator providing stimulation energy;
    (b) at least one electrode having a proximal end coupled to said signal generator and a distal end adapted to provide stimulation to a vagus nerve of a patient;
    (c) a sensor for generating a sensor signal indicative of a characteristic of a heart; and (d) control means responsive to said sensor signal for regulating said stimulation.

10. The system of claim 9 further comprising:
    (e) a switch coupled to the signal generator and operable by the patient, whereby the patient may manually turn on or off the vagus nerve stimulation.

11. The system of claim 9, further comprising:
    (e) a second sensor generating a second sensor signal indicative of a possible onset of a seizure, and wherein the signal generator is responsive to the second sensor signal.

12. The system of claim 11, wherein the second sensor is implantable to be in communication with a brain of the patient.

13. The system of claim 9, wherein the signal generated by the sensor is selected from the group consisting of an instantaneous heart rate (IHR) signal and a heart rate variability signal.

14. The system of claim 9, wherein the signal generated by the sensor is indicative of heart pulse.

15. The system of claim 9, wherein the signal generated by the sensor is of a rate of change of a heart pulse.

16. The system of claim 9, wherein the signal generated by the sensor is an electrocadiogram (EKG) of a patient.

17. A method of controlling or preventing epileptic seizures comprising the steps of:
    (a) implanting a signal generator in a body;
    (b) implanting at least one electrode to be in communication with a vagus nerve of said body;
    (c) coupling at least one electrode to said signal generator;
    (d) operating the signal generator to provide stimulation pulses to the vagus nerve via the at least one electrode;
    (e) detecting a characteristic of a heart; and
    (f) regulating said stimulation pulses in response to said step of detecting, whereby epilepsy is treated.

18. A method of minimizing effects to a heart of a patient during vagus nerve stimulation comprising the steps of:
    (a) measuring a characteristic of a heart selected from the group consisting of an instantaneous heart rate (IHR) and a heart rate variability;
    (b) determining whether the measured characteristic of the heart is within a normal range for the patient; and
    (c) if the heart is operating outside the normal range, adjusting stimulation of a vagus nerve to bring the heart within the normal range.

19. The method of claim 18, wherein the step of adjusting stimulation includes the step of adjusting at least one characteristic of stimulation pulses provided to the vagus nerve, wherein the characteristic is selected from the group consisting of pulse shape, inter-stimulus interval, pulse frequency, pulse width, pulse amplitude, and pulse phase.

20. The method of claim 18, wherein the step of adjusting includes the step of turning off stimulation to the vagus nerve.

21. The method of claim 18, further comprising the step of (d) operating a pacemaker to maintain the heart within the normal range.

22. The method of claim 18, further comprising the step of:
    (d) alerting the patient by way of a sensory signal.

23. The method of claim 22, wherein the step of alerting includes the step of providing an audio signal to the patient.

24. The method of claim 22, where in the step of alerting includes the step of providing a vibrating signal to the patient.

25. A method of minimizing effects to a heart of a patient during vagus nerve stimulation comprising the steps of:
    (a) measuring a characteristic of a heart selected from the group consisting of an instantaneous heart rate (IHR) and a heart rate variability;
    (b) determining whether the measured characteristic of the heart is within a normal range; and (c) if the heart is operating outside the normal range, alerting the patient by way of a sensory signal of effects to the heart caused by the vagus nerve stimulation.

26. The method of claim 25, wherein the step of alerting includes the step of providing an audio signal to the patient.

27. The method of claim 25, wherein the step of alerting includes the step of providing a vibrating signal to the patient.

28. The method of claim 25, further comprising the step of:
   (d) operating a pacemaker to maintain the heart within the normal range.

29. The method of claim 25, further comprising the step of:
   (d) turning off stimulation to the vagus nerve.

30. A method of minimizing effects to a heart of a patient during vagus nerve stimulation comprising the steps of:
   (a) implanting a signal generator in a body of a patient;
   (b) implanting at least one electrode to be communication with a vagus nerve of the body;
   (c) coupling the at least one electrode to the signal generator;
   (d) identifying at least one phase of a heart pulse during which vagus nerve stimulation has reduced effect on the heart; and
   (e) programming the signal generator to provide stimulation only during the at least one phase of the heart pulse.

31. The method of claim 30, further comprising the step of:
   (f) sensing an indication of a possible onset of a seizure.

32. The method of claim 31, wherein the step of sensing includes the step of sensing an electroencephalogram (EEG) of a patient.

33. The method of claim 31, wherein the step of sensing includes the step of sensing a cortical signal.

34. The method of claim 31, wherein the step of sensing includes the step of sensing an electrocadiogram (EKG) of a patient for an indication of a possible onset of a seizure.

35. The method of claim 31, wherein the step of sensing includes the step of sensing a characteristic of a heart selected from the group consisting of an instantaneous heart rate (IHR) and a heart rate variability.

36. The method of claim 31, further comprising the step of:
   (g) if a possible seizure onset is detected, providing a warning of the possible seizure onset.

37. The method of claim 36, wherein the step of warning includes the step of providing an audio signal.

38. The method of claim 36, wherein the step of warning includes the step of providing a vibrating signal.

39. The method claim 30, further comprising the steps of:
   (f) determining whether the measured characteristic of the heart is within a normal range; and
   (g) if the heart is operating outside the normal range, alerting the patient by way of a sensory signal.

40. The method claim 30, further comprising the steps of:
   (f) determining whether the measured characteristic of the heart is within a normal range; and
   (g) if the heart is operating outside the normal range, adjusting stimulation of a vagus nerve to bring the heart within the normal range.

41. The method claim 30, further comprising the steps of:
   (f) determining whether the measured characteristic of the heart is within a normal range; and
   (g) if the heart is operating outside the normal range, turning off stimulation to the vagus nerve.

42. A method of controlling or preventing epileptic seizures comprising the steps of:
   (a) implanting a signal generator in a body of a patient;
   (b) implanting at least one electrode to be communication with a vagus nerve of the body;
   (c) coupling the at least one electrode to the signal generator;
   (d) sensing an electroencephalogram (EEG) of a patient; and
   (e) operating the signal generator to enhance desynchronization of EEG rhythms.

43. The method of claim 42, further comprising the step of:
   (f) detecting a possible seizure onset; and
   (g) if the possible seizure onset is detected, providing a warning of the possible seizure onset.

44. The method of claim 43, wherein the step of providing a warning includes the step of providing an audio signal.

45. The method of claim 43, wherein the step of providing a warning includes the step of providing a vibrating signal.

46. The method of claim 42, further comprising the steps of:
   (f) measuring a characteristic of a heart selected from the group consisting of an instantaneous heart rate (IHR) and a heart rate variability;
   (g) determining whether the measured characteristic of the heart is within a normal range; and
   (h) if the heart is operating outside the normal range, adjusting stimulation of a vagus nerve to bring the heart within the normal range.

47. A method of controlling or preventing epileptic seizures comprising the steps of:
   (a) implanting a signal generator in a body of a patient;
   (b) implanting at least one electrode to be communication with a vagus nerve of the body;
   (c) coupling the at least one electrode to the signal generator;
   (d) sensing an electrocadiogram (EKG) of a patient for an indication of a possible onset of a seizure; and
   (e) if a possible seizure onset is detected, operating the signal generator to control or prevent the epileptic seizure.

48. The method of claim 47, wherein the step of sensing includes the step of sensing a heart rate.

49. The method of claim 47, wherein the step of sensing includes the step of sensing a rate of change of a heart rate.

50. The method of claim 47, wherein the step of sensing includes the step of sensing R—R variability.

51. The method of claim 47, wherein the step of sensing includes the step of sensing a rate of change of R—R variability.

52. The method of claim 47, wherein the step of sensing includes the step of sensing blood pressure.

53. The method of claim 47, wherein the step of sensing includes the step of sensing a level of oxygen saturation of blood.

54. A method of controlling or preventing epileptic seizures comprising the steps of:
   (a) implanting a signal generator in a body of a patient;
   (b) implanting at least one electrode to be communication with a vagus nerve of the body;
   (c) coupling that at least one electrode to the signal generator;

(d) sensing an electrocadiogram (EKG) of a patient for an indication of a possible onset of a seizure; and (e) if a possible seizure onset is detected, warning the patient of the possible seizure onset.

55. The method of claim 54, wherein the step of sensing includes the step of sensing a heart rate.

56. The method of claim 54, wherein the step of sensing includes the step of sensing a rate of change of a heart rate.

57. The method of claim 54, wherein the step of sensing includes the step of sensing R—R variability.

58. The method of claim 54, wherein the step of sensing includes the step of sensing a rate of change of R—R variability.

59. The method of claim 54, wherein the step of sensing includes the step of sensing blood pressure.

60. The method of claim 54, wherein the step of sensing includes the step of sensing a level of oxygen saturation of blood.

61. A system for controlling or preventing epileptic seizures comprising in combination:

(a) an implantable signal generator providing stimulation energy;

(b) at least one electrode having a proximal end coupled to the signal generator and a distal end adapted to provide stimulation energy to a vagus nerve of a patient;

(c) a sensor for generating a sensor signal indicative of a characteristic of a heart; and (d) a control algorithm responsive to the sensor signal for regulating the stimulation energy provided by the signal generator to reduce any effects to the heart.

62. The system of claim 61, further comprising:

(e) a second sensor generating a second sensor signal indicative of a possible onset of a seizure, and wherein the signal generator is responsive to the second sensor signal.

63. The system of claim 62, wherein the second sensor is implantable near a brain of the patient.

64. The system of claim 62, wherein the second sensor is implantable within a brain of the patient.

65. The system of claim 61, wherein the signal generated by the sensor is selected from the group consisting of an instantaneous heart rate (IHR) signal and a heart rate variability signal.

66. The system of claim 6 1, wherein the signal generated by the sensor is of heart pulse.

67. The system of claim 61, wherein the signal generated by the sensor is an electrocadiogram (EKG) of a patient.

68. The system of claim 61, wherein the control algorithm turns off the stimulation provided by the signal generator in response to the sensor signal indicating an undesired effect on the heart from the vagus nerve.

69. The system of claim 61, further comprising:

(e) means responsive to the sensor signal for providing a sensory stimulus to alert the patient of an undesired effect on the heart from the vagus nerve.

* * * * *